United States Patent [19]

Thomas

[11] Patent Number: 4,847,067

[45] Date of Patent: * Jul. 11, 1989

[54] MOLD AND DUST INHIBITING PRODUCT AND METHOD

[76] Inventor: Richard D. Thomas, Fullerton, Calif.

[*] Notice: The portion of the term of this patent subsequent to Feb. 21, 2006 has been disclaimed.

[21] Appl. No.: 166,077

[22] Filed: Feb. 26, 1988

Related U.S. Application Data

[60] Division of Ser. No. 27,878, Mar. 19, 1987, Pat. No. 4,770,878, which is a continuation-in-part of Ser. No. 606,150, May 2, 1984, Pat. No. 4,806,353, which is a continuation-in-part of Ser. No. 536,262, Sep. 27, 1983, abandoned.

[51] Int. Cl.$^4$ ............... A01N 37/00; A01N 59/16
[52] U.S. Cl. ................... 424/639; 424/647; 424/643; 424/678; 424/681; 424/682; 424/669; 424/649; 424/632; 424/630; 424/605; 424/601; 424/715; 424/670; 424/709; 424/650; 514/78; 514/128; 514/557
[58] Field of Search ............ 424/131, 141, 144, 147, 424/150, 154; 514/78, 128, 557

[56] References Cited

U.S. PATENT DOCUMENTS

| | | | |
|---|---|---|---|
| 3,404,987 | 10/1968 | Kooistra et al. | 424/317 X |
| 4,042,716 | 8/1977 | Bertram et al. | 424/317 X |
| 4,396,612 | 8/1983 | Candussi et al. | 514/78 |

OTHER PUBLICATIONS

"Why Glycerine For Drugs & Cosmetics"; Glycerine Producers HSSN; pp. 1,2,3, 1950.
Anderson, et al., "The Effect of Temperature Differential on the Moisture Content of Stored Wheat", *Canadian Journal of Research*, vol. 21, pp. 297-306 (1943).
Oxley, "The Movement of Heat and Water in Stored Grain", *Amer. Assn. Cer. Chem., Transactions*, vol. 6, pp. 84-100 (1948).
Disney, "The Formation of Dew on a Cooled Surface in Contact with Wheat", *J. Stored Prod. Res.*, vol. 5, pp. 281-288 (1969).
Pixton et al., "Diffusion of Moisture through Grain", *J. Stored Prod. Res.*, vol. 7, pp. 133-152 (1971).

*Primary Examiner*—Leonard Schenkman
*Attorney, Agent, or Firm*—Albert L. Gabriel

[57] ABSTRACT

A mold and dust inhibiting composition which has particular utility in connection with the storage and handling of animal feeds, grains, and hay, and also in connection with the use of animal litter such as poultry litter, as well as having general utility for controlling both mold and dust. The composition of the invention is an aqueous solution of one or more salts of propionic acid, one or more deliquescent substances, and also preferably one or more humectants. Propionate ions are made available for mold control by this solution just as effectively as propionic acid, but without the disadvantages of propionic acid including a bad odor, serious corrosive characteristics, and high volatility and hence short residual time. The deliquescent, and preferably also the humectant, prevent moisture from migrating toward container walls where there is a large day/night temperature differential, and also prevent dry regions from developing and producing potentially harmful dust. Addition of lecithin to the product as a lubricant provides additional protection against dust being generated where grain is screw-conveyed into grain elevators.

16 Claims, No Drawings

MOLD AND DUST INHIBITING PRODUCT AND METHOD

RELATED APPLICATIONS

The present application is a divisional application of Ser. No. 027,878, filed on Mar. 19, 1987, now U.S. Pat. No. 4,770,878, which is a continuation-in-part of Ser. No. 606,150, filed May 2, 1984, which in turn was a continuation-in-part of Ser. No. 536,262, filed Sept. 27, 1983 now abandoned, both prior applications being entitled MOLD INHIBITING PRODUCT AND METHOD.

BACKGROUND OF THE INVENTION

1. Field of the Invention

The present invention is in the field of mold inhibitors, and also relates to the prevention of harmful dust which is likely to be generated in the handling and use of some products which also characteristically have mold problems, such as animal feeds and grains, and poultry litter.

2. Description of the Prior Art a. Mold Problems

There is a serious worldwide problem of molds growing in food materials, and particularly in animal feeds. This problem is most serious,. and is a year-round problem, in tropical zones of both the eastern and western hemispheres, but it is also a problem in temperate and colder zones, particularly during the spring and fall seasons when there are frequently large temperature differentials between night and day, on the order of 30° F. or more, which can cause an accumulation of moisture in the feed adjacent the cold metal of feed tanks or bins.

One reason molds present such a serious problem is that they produce dangerous mycotoxins, some of which are carcinogenic. For example, one of the common molds, *Asperqillus Flavus*, produces the mycotoxin aflatoxin which, in addition to other toxic characteristics, interferes with the immune system's ability to produce gamma globulin, the protein that is part of the immune system. The resulting breakdown of the immune system then renders animals that have ingested such mold vulnerable to a variety of diseases.

The standard product that has been used for many years for the control of molds is propionic acid $CH_3CH_2COO$. Prior to the present invention, propionic acid has been the most reliable mold inhibitor for animal feeds, and it still remains the product of choice on a worldwide basis.

However, propionic acid has serious problems, so that it is unacceptable in many circumstances, and its use will be limited in some areas of the world, particularly in the Orient where the mold problem is severe. A major problem with propionic acid is that it has a terrible, strong odor, which is almost like the smell of urine, and when people work around propionic acid, their clothes and bodies acquire this obnoxious odor. One reason for this bad odor is that it is very volatile, so that it is rapidly released in vapor form from feeds to which it has been applied. For this reason, many people, and the people of some regions such as the Orient, will not stand for the use of propionic acid; and those who do use it are uncomfortable in such use. Also, some animals, particularly hogs, are especially sensitive to the odor of propionic acid.

Another serious problem with propionic acid is that it is highly corrosive. The only feasible place for propionic acid to be applied to feeds is in feed mill equipment, and this equipment is generally made of mild steel which is particularly vulnerable to acid corrosion. Thus, feed mill equipment in which propionic acid is added to the feeds will rapidly deteriorate from the attack of this acid.

A further serious problem with the use of propionic acid is that it has a high degree of volatility and hence short residual time.

A number of mold inhibitor products combining propionic acid with other ingredients such as acetic acid and benzoic acid have been and are currently being marketed under a variety of trademarks in an endeavor to make the products more commercially acceptable, but the principal operative ingredient of such products is still propionic acid, and such products still have the same problems of the odor and corrosiveness of propionic acid.

It has been understood in the art that it is the propionate ion $CH_3CH_2COO^-$ that is the active mold inhibitor ingredient in propionic acid, so attempts have been made to use salts of propionic acid as mold inhibitors in an endeavor to overcome the odor and corrosion problems. The principal salts that have been used are the sodium and calcium salts of propionic acid, and as far as applicant is aware, these have only been used as mold inhibitors in a fine, granular form, and never in the form of a liquid solution. These propionate salts do not have an objectionable odor, and are neutral and hence not especially corrosive. The sodium propionate salt has been found satisfactory in solid form for human use in bread, this being made possible because the granular or powdered sodium propionate disperses fairly well in the wet bread dough, remaining well dispersed throughout the baked bread.

Although currently used to a limited extent in animal feeds, the dry propionate salts are not satisfactory for feeds, the principal problem being that in granular form there is insufficient contact of the propionate salt particles with the grain particles unless great quantities of the propionate salts are used. On the order of five to seven times as much of the propionate salt must be used in order to disperse it adequately through the feed to get approximately the same degree of mold inhibition as can be achieved with liquid propionic acid. This makes the use of dry propionic salts such as sodium propionate and calcium propionate economically disadvantageous as mold inhibitors for animal feeds.

Prior to the present invention, propionic acid salts have never been usable in the form of a liquid solution for treating animal feeds, even though they would be equally as effective for mold inhibiting as propionic acid because it is the propionate ion which performs the mold-inhibiting function, and the liquid would be readily dispersable in intimate contact with the feed grain particles in the same relatively small amounts as with liquid propionic acid, but without the objectionable odor and corrosive characteristics of the acid. It is believed that a reason liquid propionic salt solutions have not heretofore been used as animal feed mold inhibitors is the great propensity of the propionic salts to precipitate out of the solution in a mushy, gel-like form. Even though adequate concentrations might have been achievable under controlled laboratory or plant conditions, the long-term stability would have been unreliable for a useful mold-inhibiting product.

There is also a serious mold problem which occurs in feeds stored in metal feed tanks or bins at locations where there are large overnight temperature drops, on the order of 30°–40° F., even with feeds that have a low moisture content. Such large temperature drops will lower the temperature of the container, establishing a large temperature differential between the walls of the container and the temperature of the feed within the central region of the container. Water molecules have the characteristic of moving from a warmer zone toward a colder zone, and thus will move or migrate from the central region of the container through the feed itself toward the cold walls of the container, increasing the humidity and dampening the feed near the walls to provide an excellent growing medium for molds in that region; and this is recognized as a major problem when the humidity level increases to the point where moisture actually condenses on the walls of the container. After a few repeated nights of a temperature differential on the order of 30°–40° F., mold spores which are present all of the time will become active and propagate. Even with feed having an average moisture content of 13.5 percent or less, which is normally considered to be safe from any substantial mold problem, the moisture content in the feed adjacent the container walls will be cumulatively raised higher and higher night after night of such temperature differentials, and a substantial mold problem will develop.

This same water migration problem toward cold container walls occurs in connection with the shipping of compressed hay cubes. In the overseas transportation of hay, it is common practice to compress the hay into cubes, and ship such compressed hay cubes in large batches in steel containers. For example, one company of which applicant is aware ships hay cubes in 25-ton batches per steel container. The hay is required to be relatively moist to be compressed into cubes, as for example having a moisture content of approximately 15–16 percent by weight. Large day/night temperature differentials are frequently encountered during ocean voyages, and in such case, moisture migrates from relatively warm central portions of the containers toward and onto the walls of the containers, causing the hay to get moldy adjacent the container walls.

Mold can also be a serious problem in the long-term storage of grains, as in grain elevators. It has heretofore been conventional practice to preserve stored grains from mold by dehydration prior to storage, and it is conventional practice to dry grains down to below approximately 13–14 percent moisture content by weight in preparation for storage. However, the feeding quality and efficiency of the grain is impaired when it is so dry, so that it is also conventional practice to add back moisture to the grain after it is removed from storage to improve its feeding quality and efficiency for cattle. Nevertheless, the feeding quality and efficiency of the grain still remains somewhat diminished by the grain having been subjected to the successive steps of drying and remoistening. These steps of drying and remoistening the grain are also disadvantageous because they add materially to the cost of the product.

Another mold problem of which applicant is aware associated with the handling of animals is in poultry litter. Poultry litter is conventionally composed of wood shavings, rice hulls and the like spread out to approximately a 6-inch depth under the poultry. This mold problem is most severe around the poultry feeders where moisture tends to accumulate from droppings from the birds.

b. Dust Problems

There are also serious dust problems in connection with the use, handling, and storage of some of these same materials for which there are mold problems as described above.

One such dust problem of which applicant is aware that occurs in connection with animal feeds relates to poultry feed. The tips of poultry feed granules have a tendency to dry out and break off from the feed granules and turn into dust. Such dust when breathed in by the birds can cause serious respiratory diseases such as Aspergillosis. This same problem occurs with respect to the wood shavings, rice hulls and the like used for poultry litter. The litter tends to dry out and generate dust which, when breathed in by the birds, can cause the same diseases as feed dust.

Dust has historically been a problem in connection with the storage of grains, as in grain elevators. Dust is generated by screw conveyors conventionally employed to convey grain into elevators, surface portions of the grain particles being ground off into dust. This can result in a catastrophic explosive atmosphere in a grain elevator where too much dust is generated and dispersed through the air in the elevator. This problem is compounded where the grain is dried prior to storage as a mold-preventing measure. Some fat is frequently applied to grain in the screw conveyors to lubricate surface portions of the grain against being ground off into dust, but its utility tends to be diminished by absorption of the fat internally into dry granules.

c. Other Problems

Another problem in the handling of animal feed is that it tends to cake and "bridge." Moisture from inside the body of feed appears to migrate to a location proximate the walls of the feed bins, including the bin gate. Also, respiration appears to occur in the grain from poor air circulation resulting from such moisture, causing a spontaneous heating and generation of further moisture as a byproduct of the respiration. Accumulation of such moisture causes the caking and bridging to occur, and this blocks the flow of feed when the gate is opened. This is such a widespread problem that a rubber mallet is placed next to most feed bins in the United States so that the caking and bridging can be shattered by striking the wall of the bin to start the grain flowing.

A further problem relating to feed grains is that very hard grains such as corn are conventionally rolled with the addition of steam so as to convert them into a flake form. A "conditioner" is conventionally applied with the steam to assist the absorption of moisture into the grain and thereby reduce the amounts of mechanical power and steam required in the rolling process, and hence reduce the cost.

SUMMARY OF THE INVENTION

In view of these and other problems in the art, it is a general object of the present invention to provide a liquid mold inhibitor that is as effective as propionic acid, but does not have the objectionable odor, corrosion problems, and high volatility and hence short residual time characteristic of propionic acid, and which is therefore particularly useful for controlling mold in animal feeds and grains.

Another general object of the present invention is to provide a liquid mold inhibitor which, because of its effectiveness and lack of objectionable characteristics, will be acceptable in all areas of the world, and most importantly, in those tropical areas where mold is a serious problem but propionic acid will often not be used because of its bad odor and corrosive characteristics.

Another object of the invention is to provide a liquid mold inhibitor which comprises an aqueous solution of a salt of propionic acid, which may be one or more of three propionate salts, ammonium propionate, sodium propionate, and potassium propionate.

Another object of the invention is to provide a propionate salt solution mold inhibitor which includes deliquescent material, preferably one or more deliquescent substances from the group consisting of magnesium chloride, calcium chloride, manganese chloride, ferric chloride, and zinc chloride, the deliquescent material holding water in the treated product to maintain hydrolyzation and hence effectiveness of the propionate ion content of the treated product, and serving the surprising function of preventing treated materials such as feed, grain, and compacted hay from becoming overly damp near the walls of containers subject to large overnight temperature differentials.

Another object of the invention is to provide a liquid propionate salt solution mold inhibitor of the character described which includes one or more humectants, preferably from the group consisting of glycerol, potassium polymetaphosphate, propylene glycol, sorbitol, triacetin, mannitol, pectins, and polyhydric alcohols, the humectant trapping odor-carrying moisture molecules in the liquid solution, and also cooperating with the deliquescent material in keeping the water content of the solution up so that the propionate salt remains fully hydrolyzed and thereby fully functional as a mold inhibitor, and additionally cooperating with the deliquescent material in preventing water molecules from migrating through containers and concentrating proximate cold container walls.

A further general object of the invention is to provide a novel aqueous mold-inhibiting solution which also surprisingly and synergistically has excellent dust-inhibiting characteristics, whereby the same aqueous solution of the invention when applied to feeds, grains, hay, poultry litter or the like will function to either inhibit the formation and propagation of mold or inhibit the formation of dust, and under some circumstances, will perform both of these inhibiting functions with respect to a product treated by the invention.

A further, more specific object of the invention is to provide an aqueous solution containing one or more salts of propionic acid, one or more deliquescent substances, and also preferably one or more humectants, which will function both to prevent the growth of mold and prevent the production of dust with respect to treated products.

A still further object of the invention is to provide a mold and dust inhibiting aqueous solution of the character described which, while protecting poultry feed and poultry litter against mold, also protects both poultry feed and poultry litter against the formation of dangerous dust which, when breathed in by birds, may cause a respiratory disease such as Aspergillosis.

Another object of the invention is to provide a mold and dust inhibiting aqueous solution which, when applied to grain, will protect the grain against mold during storage, and will also protect the grain against the production of potentially explosive dust when screw-conveyed into grain elevators for storage.

Another object of the invention is to enhance the dust inhibiting function of the liquid product of the invention, particularly where the invention is to be used on grain that is to be screw-conveyed into storage, by including a uniformly dispersed suspension of feed-grade lecithin in the aqueous solution of the invention, the lecithin lubricating the grain against the production of dust by abrasion in the screw conveyor.

Another object of the invention is to provide a dust and mold inhibiting aqueous solution product of the character described which also functions as a conditioner for reducing the amount of mechanical power and steam required in the steam rolling of hard grains such as corn.

Another object of the invention is to provide a mold and dust inhibiting product of the character described which serves the further function of preventing caking and bridging of animal feeds.

An additional object of the invention is to provide a mold and dust inhibiting product which functions over a long residual time.

The product of the present invention is an aqueous solution of one or more salts of propionic acid and deliquescent material, and preferably also humectant. The salt of propionic acid may be ammonium propionate, sodium propionate, or potassium propionate, or any combination of these three propionate salts. The deliquescent material may be one or more of a large number of deliquescent substances as set forth hereinafter in the Detailed Description, but is preferably one or more deliquescent substances from the group consisting of magnesium chloride, calcium chloride, manganese chloride, ferric chloride, and zinc chloride. The humectant is preferably one or more humectant substances from the group consisting of glycerol, potassium polymetaphosphate, propylene glycol, sorbitol, triacetin, mannitol, pectins, and polyhydric alcohols. The pH of the aqueous solution of the invention is preferably in the range of from approximately 6.3 to approximately 6.9, which is a substantially neutral condition of the aqueous solution. Such substantially neutral condition minimizes the volatility of the propionate ion content of the solution, and thereby helps keep odor to an absolute minimum, while at the same time the propionate ion content of the solution is fully effective for mold control, being just as effective as propionic acid. Because of this substantially neutral condition of the solution of the invention, it is generally noncorrosive, having corrosive characteristics approximating those of water.

The deliquescent material in the aqueous solution of the invention stops water from coming off of the treated product, maintaining hydrolyzation of the propionic salt and hence effectiveness of the propionate ion content for inhibiting the propagation of mold throughout the product that is treated. At the same time, it is believed that by stopping water from coming off of the treated product, the deliquescent material thereby also stops propionate ions from coming off with the water vapor, which would otherwise tend to shorten the residual time or effective operating life of the solution of the invention and also tend to cause objectionable odor. The presence of the deliquescent material in the solution of the invention also prevents dry surface areas from developing in products treated by the invention, such as feeds, grains, and poultry litter, and thereby prevents the generation of potentially harmful dust from the treated products.

The humectant which is also preferably included as a component of the aqueous solution of the invention cooperates with the deliquescent material in stopping water from coming off of the product, and hence in maintaining hydrolyzation of the propionic salt, blocking both water molecules and propionate ions from coming off of the treated materials, and in preventing the development of dry, dust-producing areas of the treated materials.

While odor control is primarily accomplished by use of propionate salt instead of propionic acid, and also by the substantially neutral condition of the solution which minimizes volatility of the propionate ion content, odor control is also aided by the water molecule-attracting power of the deliquescent material, and where humectant is included in the solution, the humectant further controls odor by inhibiting the moisture molecules from escaping the liquid solution and thereby locking odor-carrying moisture in the solution.

Where feed, grain, hay or the like is to be kept in a closed metal tank, bin, or other container, the presence of deliquescent material in the solution of the invention has the surprising and unexpected result of greatly reducing the propagation of mold in such containers that are subject to large day/night temperature drops by preventing moisture from migrating toward cold container walls and accumulating in the treated materials adjacent the walls. Presence of humectant in the solution of the invention cooperates with the deliquescent material in such stabilization of the location of the water molecules throughout the container.

Another surprising and unexpected function of the solution of the invention is that when it is applied with steam for the steam rolling of grains such as corn, it acts as an excellent "grain conditioner" to considerably reduce the amount of mechanical power and steam required for such operation, and thereby reduces the cost of the operation. The solution of the invention has the still further surprising and unexpected function of preventing the usual caking and bridging of feeds, eliminating the need to whack the feed bin with a mallet to start it flowing out of the gate.

An additional ingredient that may be included in the solution of the invention is a substantially uniform dispersion of feed-grade lecithin, which serves to lubricate grain surfaces and thus cooperate with the already generally uniform dampness preserved in grain by the presence of deliquescent material, and also preferably humectant, in minimizing the generation of dust when grain is transported into grain elevators by means of screw conveyors.

A still further ingredient that may be included in the solution of the invention, particularly where the solution is to be used on feed intended for hogs is monosodium glutamate.

DETAILED DESCRIPTION

The product of the invention is a mold and dust inhibiting aqueous solution which finds particular utility in connection with the storage and handling of animal feeds, grains, and hay, and also in connection with the use of animal litter such as poultry litter, as well as having general utility for controlling both mold and dust where humidity and temperature conditions are such as to make these a problem.

Mold problems in connection with animal feeds, grains, and hay are conventionally thought of as only being present in damp, humid climates. However, applicant has determined that where feeds, grains, or hay are stored or transported in metal bins or containers, regardless of the humidity wide temperature variations which are likely to occur between day and night will often cause moisture migration toward and onto the walls of such bins and containers, producing a peripheral concentration of moisture which is conducive to mold propagation.

Dust problems relative to feeds, grains and the like are conventionally regarded as dry, low humidity climate problems, and those having ordinary skill in the art would not consider the possibility that a product such as the present invention which has particular utility for the control of dampness-propagated mold might also have particular utility for the control of dust. In the present invention, the novel combination of ingredients not only effectively controls the propagation of mold, but at the same time, performs what would normally be considered an opposite function of effectively controlling dust, and the present invention is desirably applied to batches of feeds, grains, and hay to inhibit and control mold propagation and/or dust production regardless of what environments such batches may be subjected to, and therefore without any need for selectively applying separate mold inhibiting and dust inhibiting measures to such batches according to projected environments or handlings to which the batches may be subjected.

The principal combination of the invention is an aqueous solution of a salt of propionic acid, which is preferably ammonium propionate, sodium propionate, or potassium propionate, or any combination of these, together with a deliquescent material, which is preferably one or more deliquescent materials from the group consisting of magnesium chloride, calcium chloride, manganese chloride, ferric chloride, and zinc chloride. The invention also preferably includes one or more humectants from the preferred group consisting of glycerol, potassium polymetaphosphate, propylene glycol, sorbitol, triacetin, mannitol, pectins, and polyhydric alcohols.

Moisture control in the material to which the invention is applied is accomplished primarily by the presence of the deliquescent material, and involves stabilization of moisture in the product to which the invention is applied, both against evaporation and against movement or migration of water molecules, as described hereinafter in detail. When humectant is combined in the product of the invention, it cooperates with the deliquescent material in controlling moisture against evaporation and migration by blocking the escape of water molecules from the protected product, and is also particularly useful in controlling odor which has historically been a serious problem where propionic acid has been used for mold control.

Applicant's aqueous solution of one or more salts of propionic acid and one or more deliquescent materials, and also preferably one or more humectants, serves both of the primary inhibiting functions of the invention, namely, mold inhibiting and dust inhibiting. Nevertheless, as further assurance against the production of potentially explosion-causing dust in the screw-feeding of grains such as corn into grain elevators, it is also preferred to include a fatty material, preferably feed-grade lecithin, as a substantially uniformly dispersed suspension in the aqueous solution, the lecithin or other fatty material cooperating with the other ingredients as a positive assurance against the production of dust in this situation.

An additional ingredient that may be included in the aqueous solution of the invention, particularly where the solution is to be used on feed intended for hogs, is monosodium glutamate (MSG).

By employing one or more salts of propionic acid instead of the state-of-the-art mold inhibitor propionic acid per se, the solution of the present invention is enabled to be made close to neutral, with a preferred pH of approximately 6.6, and a preferred pH range of from approximately 6.3 to approximately 6.9, instead of highly acidic as is propionic acid, and this in turn makes the solution much less volatile than propionic acid, which reduces the odor, and also makes the solution generally noncorrosive, having corrosive characteristics approximating those of water. A series of factors which determine this preferred pH and preferred pH range are described in detail hereinafter. The salt or salts of propionic acid embodied in the invention nevertheless have substantially the same mold-inhibiting effectiveness as propionic acid, but without its three major objectionable features, namely, disagreeable odor, highly corrosive characteristics, and high volatility and hence short residual time. Thus, the propionate salt component of the present invention gives the invention the same utilitarian capability as propionic acid, without its objectionable features, and thereby makes the invention acceptable for mold control in all areas of the world, and most importantly in those humid tropical areas where mold is a severe problem but propionic acid will not be used because of its bad odor, corrosive characteristics, and short residual time.

While all three salts of propionic acid, sodium, ammonium, and potassium, or any combination of the three, are satisfactory for the present invention, as will be appreciated from test data set forth hereinafter, ammonium propionate is presently preferred because for a selected percentage by weight of the deliquescent material or materials in the formulation, a relatively greater, and hence more effective, percentage by weight of propionate ions can be included in the formula. Next preferred is potassium propionate, because for a selected percentage by weight of deliquescent material, the next largest percentage by weight of propionate ions can be included in the formula. Least preferred of the three propionate salts is sodium propionate, because for a selected percentage by weight of deliquescent material, the least percentage by weight of propionate ions can be included in the formula of the three propionate salts.

For similar reasons, the most preferred deliquescent materials from the preferred group consisting of magnesium chloride, calcium chloride, manganese chloride, ferric chloride, and zinc chloride, are magnesium chloride, ferric chloride, manganese chloride, and zinc chloride, while the least preferred of these five deliquescent materials is calcium chloride. For a selected percentage by weight of these preferred four deliquescent materials, a larger percentage by weight of effective propionate salt is enabled to be included in the formula than can be included where calcium chloride is the selected deliquescent material. Test data supporting such selection is set forth in detail hereinafter.

Of the preferred group of humectants consisting of glycerol (glycerine), potassium polymetaphosphate, propylene glycol, sorbitol, triacetin, mannitol, pectins, and polyhydric alcohols, the presently preferred humectant is glycerol because of its widespread availability and acceptance as a food ingredient.

The presence of the deliquescent material in combination with the salt of propionic acid in applicant's aqueous solution provides a plurality of cooperative functions which, at least in part, are unexpected and surprising, and contrary to what those skilled in the art would expect. The strong attraction of the deliquescent component of the invention effectively stops water from evaporating from or coming off the feed, grain, hay, poultry litter, or other treated product to which the present invention has been applied. (1) Thus, the deliquescent material prevents a reduction of moisture in the treated product which would in turn reduce hydrolyzation of the propionate salt which is necessary for maintaining the active condition of the propionic ions for performing the mold inhibiting function. (2) Also, the deliquescent material in the solution of the present invention bars evaporation of water molecules from relatively warm zones in feeds, grains, hay and the like, and migration of such evaporated water molecules toward relatively cold zones such as feed bin or container walls under climatic conditions where there is a relatively large temperature differential between day and night, preventing moist, mold-propagating zones from being generated adjacent container walls during storage and transport of such treated materials. (3) Further, it is believed that the deliquescent material, by inhibiting escape of water vapor from the treated products, stops propionate ions from coming off of the treated products with water vapor which would reduce the propionate concentration and hence the mold-inhibiting strength of the treatment, and which would also tend to cause objectionable odor. (4) Presence of the deliquescent material in the solution of the invention prevents dry, dust-producing surface zones from developing on feeds, grains, poultry litter and the like by evaporation of moisture from such surface portions, preventing the production of dust which might be harmful when breathed in by animals such as poultry, or which might result in calamitous, explosive atmospheres in storage regions such as grain elevators. (5) Further, the deliquescent material tends to equalize moisture or make moisture more uniform throughout the treated product by providing a relatively greater affinity for moisture in relatively drier regions of the product than in relatively wetter regions of the product, tending to reduce unwanted zones of high moisture concentration such as in litter under poultry feeders, minimizing mold-propagating moisture concentrations.

The deliquescent material serves a completely new and unexpected function in the art where feeds and grains are kept in metal tanks or bins, which is a widespread practice. This function is the opposite of what those skilled in the art would expect the function of a deliquescent material to be. Deliquescent materials are well known to have a strong attraction for moisture, and for this reason it would be expected that the deliquescent material in applicant's solution would simply draw in moisture from the air trapped in the metal feed bin each time the cover of the bin was opened and then reclosed, and thereby raise the moisture level within the feed and in due course increase the moisture to a level at which the feed may be vulnerable to the propagation of mold.

The new function of the deliquescent material in combination with the mold-inhibiting propionate salt in applicant's solution is based upon a problem which develops in feed bins located in climates where there is a large nighttime temperature drop, on the order of 30°–40° F., which is the case in many climates particularly during the spring and fall seasons. The large overnight drop in temperature of the metal of the feed bin causes large numbers of water molecules to move from the generally warm interior of the mass of feed within the bin toward the cold metal walls of the bin, thereby increasing the dampness of the feed adjacent the walls of the bin. To illustrate this characteristic of water molecules moving from a warmer region toward a cold surface, attention is directed to the fact that considerable amounts of water will almost always condense on the exterior of a glass containing an iced drink, even though the air in that region may seem to be relatively dry.

It is generally recognized in the art that if the moisture content of feed can be kept down to a level of 13.5 percent or less by weight, there will be no substantial mold problem. However, even if the average moisture content of the feed in a bin is only 13.5 percent, after a few successive nights during which the overnight temperature drop is on the order of 30–40° F., cumulative movement of water molecules through the feed from the central region toward the walls of the bin will raise the moisture content of the feed near the walls to a much higher percentage than the original 13.5 percent or less average water content, creating a substantial mold problem in the peripheral regions of the bin. When the moisture movement to the walls of the bin reaches the stage where moisture is visibly condensing on the inside of the walls of the bin, then it is recognizable as a major mold problem.

There is a surprisingly large quantity of water available in feed for such movement of water molecules toward the walls of feed bins, even with a moisture content of the feed down to the 13.5 percent level generally considered safe against mold. Thus, at 13.5 percent moisture content, a 52 lb. bushel of feed contains 7.06 lbs. of water, which is approximately 3.5 quarts. If the 52 lb. bushel contains 16 percent moisture, which is typical for corn that is shipped, then this amounts to 8.32 lbs. of water, or approximately one gallon. To appreciate the tremendous number of water molecules involved in the problem of movement thereof toward the walls of feed bins, 7.06 lbs. of water, the amount in one bushel of feed at 13.5 percent moisture content, according to Avogadro's Number (1 molecular weight of any substance contains 6 times $10^{23}$ molecules), the 7.06 lbs. of water would contain 1.06 times $10^{26}$ water molecules, or 106 trillion trillion molecules of water. It will thus be seen that a very large amount of molecular traffic of water molecules can be caused to occur through a feed bin in response to a large overnight temperature drop.

This water molecule migration through the feed toward the walls of the bin has, surprisingly, been overcome by the presence of the deliquescent material in the product of the invention. The product, including the deliquescent material, is substantially uniformly distributed throughout the body of feed in the bin, and the deliquescent material has a greater affinity for all of the water molecules throughout the feed than the temperature differential attraction of the cold surfaces of the walls of the bin, so that the water molecules are substantially restrained from the usual and expected movement toward the cold walls of the bin for all temperature fluctuations that would normally be expected. As a result, with the product of the invention generally uniformly distributed throughout the feed, there is no observable increase in the moisture content of the feed adjacent the walls of the bin as compared with the moisture content of the feed throughout the remainder of the bin, and consequently there is no increased mold problem adjacent the walls of the bin. The humectant that is preferably included as an ingredient of the product of the invention, and hence is also substantially uniformly dispersed throughout the feed, cooperates with the deliquescent material in holding the water molecules against movement toward cold walls of the bin because the attraction the humectant has for OH groups tends to block the escape of water from the feed throughout the body of the feed in the bin.

Thus, applicant's new combination of propionate salt and deliquescent material in aqueous solution, preferably also including humectant material, when generally uniformly applied throughout a body of feed, not only serves the basic function of inhibiting propagation of mold throughout the body of the feed, but additionally serves the cooperative new and unexpected function of blocking the migration of water molecules from a relatively warm interior body of the mass of feed toward relatively cold walls of the container for the feed.

Despite the effectiveness of the product of the present invention in preventing water molecule migration toward relatively cold bin walls, the presence of the product of the invention throughout the feed has not been found to materially increase the overall moisture content of feed from air trapped in feed bins when the covers of the bins are repeatedly opened and reclosed, even over a considerable period of time. It is believed that this is because only a relatively small quantity of the product of the invention relative to the quantity of feed is required for the invention to satisfactorily perform its mold-inhibiting and water anti-migration functions, as for example an amount of only approximately 2–7 lbs. of the present product per ton of feed as discussed hereinafter; and also because there is preferably only a relatively small percentage by weight of the deliquescent material contained in the product of the invention, preferably not more than approximately 10 percent deliquescent material.

The above-described water anti-migration function of the invention is not only applicable to animal feeds, but is equally applicable in the storage or transport of any grains where day/night temperature differentials will cause relatively large temperature changes in the walls of the containers for the grains. Actually, the water anti-migration function of the invention is applicable to any material which is protected against mold by having the solution product of the invention applied thereto. An example of another material to which the invention is beneficially applicable for mold inhibiting and associated water anti-migration is hay which is currently being shipped by sea in compressed cubes transported in large steel containers. In many shipping areas there is a large day/night temperature differential. This is a particularly severe problem in shipments from the United States to the Orient, where the containers are sometimes on shipboard for 2–3 weeks with hot days and relatively cold nights. While conventionally some materials such as grains are dried as an anti-mold measure, approximately 15–16 percent moisture content is required for compressing the hay cubes, and prior to use of the present invention, there has been a serious mold problem in the shipping of such compacted hay cubes, the moisture from within the containerized batch of cubes migrating toward the container walls because of the day/night temperature differential, thereby increasing the moisture level near the container walls to one which is conducive to mold propagation. The combined mold-inhibiting and water anti-migration functions of the invention provide a complete solution to this problem.

While the presently preferred deliquescent material is one or more deliquescent substances from the group consisting of magnesium chloride, calcium chloride, manganese chloride, ferric chloride, and zinc chloride, nevertheless the deliquescent material may be any one or more deliquescent chemicals from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, magnesium chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

The humectant or combination of humectants preferably included in the product of the present invention have the characteristic of opposing or blocking escape of water molecules from materials to which the present invention is applied, such as feeds, grains, or poultry litter, and by virtue of such function, the humectant or humectants cooperate with the deliquescent material in maintaining hydrolyzation of the propionic salt, avoiding the development of dry zones in the treated material, preventing evaporation of moisture from relatively warm zones so that it might be able to migrate to relatively cold zones, and in preventing propionate ions from coming off with water vapor which would tend to reduce the mold-inhibiting strength of the product and also tend to cause odor from released propionate ions.

The great reduction of odor achieved by the present invention appears to be the result of a synergistic cooperation between the substantial neutralization of propionic acid and the presence of both the deliquescent component of the solution and the humectant component of the solution. The substantially neutral propionic salt solution has a much lower volatility than propionic acid, which greatly reduces the evaporation of odor-carrying moisture to a sufficiently low level for the deliquescent material and the humectant to be able to substantially completely "lock in" the odor. A humectant has heretofore been used by applicant for control of evaporation, but applicant is not aware of any prior use of a humectant, or of a deliquescent material, coupled with neutralization for odor control, or of any such use for animal feed. In applicant's prior U.S. Pat. No. 4,008,332, issued February 15, 1977 for "Microcide," a humectant and a deliquescent were used to prevent evaporation of a very thin film of microcide-containing moisture on a relatively short-term basis, unrelated to odor control.

The propionate salt solution of the present invention is produced by mixing propionic acid with base which may be ammonium hydroxide, sodium hydroxide, potassium hydroxide, or a mixture of any two or more of these three bases. The quantity of base relative to the propionic acid is adjusted to provide the desired pH. The pH of the present mold-inhibiting product solution is preferably in the range of from approximately 6.3 to approximately 6.9, which, although slightly acidic, is a substantially neutral state. The presently preferred pH for the product of the invention is approximately 6.6. There is a series of factors which form the basis for such preferred and most preferred pH ranges for the present invention. One such factor is that applicant has found that this preferred range is optimal for the effectiveness of propionic acid salt in controlling most molds. The propionic acid salt disassociates with maximum effectiveness in the aqueous solution within the pH range of approximately 6.3 to approximately 6.9, and it is the propionate ion which does the job of mold control. A second factor that applicant has found in having his preferred range of pH from about 6.3 to about 6.9 is that within this range, the solution is not substantially more corrosive than water, and this is important because the aqueous solution of the present invention is primarily applied to vegetable materials such as feeds and grains housed in mild steel containers. A third factor of importance in selecting applicant's pH range where the product of the invention is to be applied to animal feeds is palatability. The taste of the feed to which the product is applied is considerably better within the applicant's range than if the acidity of the product goes much below a pH of approximately 6.3. A fourth factor of importance relative to pH is that the lower the pH below approximately 6.3, the more volatile the propionate ions become, with consequent evaporation and loss of strength of applicant's solution for its intended purpose of mold inhibition, and also increased odor.

The ability of the liquid product of the invention to effectively inhibit the production of dust in connection with the use and handling of feed, grains, and poultry litter is a surprising and synergistic functional addition to the mold-inhibiting capability of the product. The dust-inhibiting function of the product is important in several specific environmental situations of which applicant is aware. There are two separate sources where dust is commonly generated in the production of poultry. First, the tips of poultry feed particles dry and break off into dust, and this is breathed in by the birds and is a common cause of respiratory disease problems such as Aspergillosis. A separate source of dust which is a common cause of these same diseases in birds is poultry litter, which is generally in the form of wood shavings, rice hulls and the like. The litter is periodically rototilled, but nevertheless areas of the litter commonly dry out and become dusty, and when such dust is breathed in by the birds, it is likely to cause respiratory diseases such as Aspergillosis. When the poultry feed and litter are sprayed with the liquid product of the invention, the deliquescent material in the product, and also preferably the humectant in the product, cause the moisture to be locked into the product, preventing moisture from evaporating off of surface portions of the feed and litter. The result is that dust cannot be generated from the feed or litter. At the same time, the liquid product of the invention protects the feed and litter against mold where conditions are such that mold might otherwise propagate.

It is conventional practice to dry feeds and grains before they are put into storage, so as to avoid the likelihood of mold formation while the products are being stored. Typically, feeds and grains are dried down to below approximately 13-14 percent moisture by weight. However, the feeding quality of such products is materially reduced by such drying, and it is therefore also conventional practice to add back moisture in order to improve the feeding quality or efficiency for cattle when the products are ready for use. Such drying of feeds and grains for storage, and then remoistening them for consumption add to the cost of the products. When feeds and grains are treated with the liquid product of the present invention, the mold-inhibiting effectiveness of the invention makes such drying for storage and remoistening unnecessary. For example, in tests conducted under applicant's direction, corn was picked at approximately 19 percent moisture content, treated with the liquid product of the invention, and then stored for a whole year, and there was no observable mold formation in the treated corn.

Another very serious dust problem in connection with the handling of grains is the production of relatively large quantities of dust from surface abrasion during the screw conveyor feeding of grains into grain elevators. The potentially catastrophic seriousness of this problem is illustrated by the fact that nine grain elevators blew up from dust explosions in the United States in 1985. This problem is compounded by the fact that grains are conventionally dried before being stored in elevators, the dry surfaces of the grain particles more readily being abraded into dust in screw conveyors. Treatment of the grain before storage with the liquid product of the present invention causes moisture to be retained in the surfaces of the grain particles, and as aforesaid, also eliminates the need for drying before storage, so that surface abrasion and consequent dust production is greatly reduced by use of the invention.

Because of the seriousness of the grain elevator dust problem, it is conventional practice to spray the grain with ¼ to ½ of fat per ton of grain as the grain goes up the screw conveyor, the purpose of the fat being to grease the surfaces of the grain particles to minimize grinding surfaces off into dust, and to trap what dust may be present. Because of the dryness of the grain, particularly in the outer regions of the granules, the fat tends to be absorbed into the grain particles and its surface utility thereby diminished.

As indicated above, treatment of the grain with the liquid product of the invention reduces the formation of dust in handling of grains such as when they are screw-conveyed into grain elevators, both by maintaining moisture in surface regions of the grain and by eliminating the need for drying the grain before storage as an anti-mold measure.

Applicant has discovered that a sufficient proportion of feed-grade lecithin can be uniformly dispersed in the aqueous solution of the invention to perform the surface lubricating function conventionally accomplished by adding fats to grains. Lecithin is a waxy phospholipid or phosphatide, and applicant has found that up to one part feed-grade lecithin to four parts of applicant's liquid product can be uniformly dispersed in colloidal suspension in the aqueous solution. The feed-grade lecithin has three advantages over fats commonly used. First, it is commonly understood to have better nutritional value. Second, it does not require a separate emulsifier to be placed in a stable, uniformly dispersed suspension in the aqueous solution of the invention. Third, lecithin is a hygroscopic substance, and therefore tends to cooperate with the deliquescent material and humectant in their moisture and odor control functions.

If a fatty substance other than lecithin is embodied in the aqueous solution of the invention to assist in dust suppression, it will normally require use of a conventional emulsifying procedure in order to be placed in uniformly dispersed suspension in the solution.

The dust problem pertaining to poultry litter and the solution of such problem by use of the present invention were described above. There is also a mold problem in the use of poultry litter, which is conventionally wood shavings, rice hulls and the like, in general around feeders where liquid excrement tends to accumulate. Substantially uniform application of the liquid product of the invention to poultry litter completely solves this problem by the strong mold-inhibiting quality of the invention. The excellent odor control characteristic of the invention while important in feed so that the feeds will not be objectionable to animals, is also important in the use of the invention with poultry litter because the large area over which the litter is spread and the fluffy, porous nature of the litter exposes a very large overall surface area to the atmosphere within the confines of the poultry housing area. Use of the conventional propionic acid mold inhibitor for this purpose would be virtually impossible because of the terrible odor which would accumulate. Despite such large exposed surface area of poultry litter, the moisture retention and odor suppression characteristics of the invention enable excellent mold-inhibiting characteristics to be maintained over an extended useful life of the litter without objectionable odor from the product of the invention.

With the product of the invention substantially uniformly dispersed throughout the litter, the invention tends to maintain a generally uniform moisture distribution throughout the litter. Where added moisture tends to accumulate around feeders, the mold-inhibiting quality of the invention has been found with repeated applications of the invention to be strong enough to prevent formation or propagation of mold in such regions.

Feed grain such as corn is conventionally rolled with the addition of steam, and to reduce the amount of mechanical power and steam required, a "grain conditioner" is often added with the steam to cause the moisture to be better absorbed in the grain, enabling the grain to be more readily broken down. In tests conducted during the steam-rolling of corn, the liquid product of the invention was added simultaneously with the application of the steam so as to embody the invention in the corn for its normally intended use as a mold and dust inhibitor. Surprisingly and unexpectedly, the product of the invention served as a better conditioner than conventional conditioners, greatly reducing the mechanical power and amount of steam required, and resulting in production of better grain flakes than are conventionally producible. The presence of the product of the invention appears to make the moisture from the steam penetrate the grain more rapidly and uniformly for easier breakdown of the grain. For this "grain conditioner" function of the invention, it is preferable to add the liquid product of the invention concurrently with the steam.

Except when the product of the invention is applied directly with steam for steam rolling of grain, the liquid product of the invention is preferably substantially uniformly applied to the feed at the feed mill, preferably being applied in the mixer when the feed is being mixed. Such application can conveniently be made by use of a metering pump, the input end of which is placed in a drum containing the liquid product of the invention, and the output end leading through a manifold which sprays the liquid product of the invention onto the feed. In feeds which contain molasses, a convenient way of applying the liquid product of the invention is to mix it into the molasses before the molasses is added to the feed.

Another problem which has been surprisingly and unexpectedly solved by the present invention in the handling of feeds is what is commonly referred to as the "bridging" of feed. Feed has a tendency to get damp and to cake and bridge in feed bins, blocking the flow at bin gates, and this problem is so universal that almost every fed bin in the United States has a rubber mallet standing beside it which is used to whack the feed bin wall to break up the caking and bridging so as to get the feed flowing through the gate. Associated with this caking and bridging is a spontaneous heating which is sometimes observable in cold weather by steaming of the feed. This is believed to be caused by respiration in the grain involving conversion of soluble carbohydrate to heat and water, which represents a loss in the nutritional value of the feed. Surprisingly, where the feed has been substantially uniformly treated with the aqueous product of the invention, such caking and bridging, and spontaneous heating, do not occur, and it is no longer necessary to start the feed flowing at the gate by hitting the bin with a mallet. It is theorized that with the presence of the invention product distributed throughout the body of feed in the bin, moisture is not enabled to migrate and thereby produce such caking and bridging. It is also theorized that the caking and bridging block ventilation which otherwise occurs through the loose feed, and without air circulation the spontaneous respiration is likely to occur. The moisture generated in the spontaneous respiration or combustion process appears to be an integral part of the caking and bridging process, in that it continuously adds to the moisture present proximate the gate, which in turn tends to make the feed particles stick more and more tightly together as the process proceeds.

Applicant has found that to assure long-term protection against mold and dust in most environments, 2–4 lbs. per ton of the liquid mold and dust inhibitor of the invention should be used for a moisture content of feed and grain up to 14 percent by weight; and that for every 2 percent increase in moisture over 14 percent, one, lb. per ton more of the product should be added. Thus, 3–5 lbs. per ton of the product should be used for a moisture content of 14–16 percent, 4–6, lbs. per ton for a moisture content of 16–18 percent, and 5–7 lbs. per ton for a moisture content of 18–20 percent. For severe mold problems, considerably more of the product of the invention may be desirable. For example, in the most severe grain mold problem of which applicant is aware, that of brewers wet grains, it may be desirable to use up to approximately 10 lbs. of the liquid product of the invention per ton of wet grains. In an experiment with brewers wet grains, which normally start to mold within about 24 hours, applicant employed 10 lbs. per ton of the liquid product of the invention, and after three weeks of observation, there was no mold whatsoever observable.

Where feed-grade lecithin is employed in suspension with the invention, that will represent an additional weight of product per ton of feed, preferably approximately one part by weight of lecithin to four parts by weight of the liquid product of the invention.

Limits and Proportions of the Ingredients

Upper Limits for Propionate Ions

In the following description, percentages by weight for propionate ion content in solutions of the invention are given as percentages by weight equivalent of propionic acid, of which 98.65 percent by weight is propionate ion.

In general, it is preferred that close to the maximum possible propionate ion content be provided in the product of the invention for maximum effectiveness in the function of mold inhibition, while still being a totally stable product under forseeable weather conditions (i.e., no material amount of the product being likely to precipitate out), and at the same time, enabling the presence of sufficient deliquescent material for efficient operation of the product both as a mold inhibitor and as a dust inhibitor, which includes efficient operation of the product in its water anti-migration function.

2.7 percent by weight is a desirable percentage of deliquescent material for a highly effective product according to the invention, being a sufficient amount to assure against loss of moisture and consequent dust problems in very dry climates and to assure against moisture migration where there are likely to be very wide day/night temperature variations and moisture migration would otherwise be serious problem. With 2.7 percent by weight deliquescent material, where the salt of propionic acid is ammonium propionate, the maximum weight equivalent of propionic acid (of which 98.65 percent by weight is propionate ion) which applicant has been able to place in a stable solution of the invention is:

59% with calcium chloride as the deliquescent;
68% with magnesium chloride as the deliquescent;
68% with ferric chloride as the deliquescent;
68% with manganese chloride as the deliquescent;
68% with zinc chloride as the deliquescent.

With sodium propionate as the salt of propionic acid, for 2.7 percent by weight deliquescent material, the maximum percent by weight equivalent of propionic acid (of which 98.65 percent by weight is propionate ion) which applicant has been able to place in a stable solution of the invention is:

30% with calcium chloride as the deliquescent;
68% with magnesium chloride as the deliquescent;
68% with ferric chloride as the deliquescent;
68% with manganese chloride as the deliquescent;
68% with zinc chloride as the deliquescent.

Where the salt of propionic acid is potassium propionate, for 2.7 percent by weight of deliquescent material, the maximum percentage by weight equivalent of propionic acid (of which 98.65 percent by weight is propionate ion) which applicant has been able to place in a stable solution of the invention is:

41.7% with calcium chloride as the deliquescent;
62.4% with magnesium chloride as the deliquescent;
68% with ferric chloride as the deliquescent;
62.4% with manganese chloride as the deliquescent;
56.8% with zinc chloride as the deliquescent.

Applicant's testing indicates that where a combination of two or more of the ammonium, sodium and potassium salts of propionic acid is employed, and where a combination of two or more of the deliquescents calcium chloride, magnesium chloride, ferric chloride, manganese chloride, and zinc chloride is employed, the amounts of propionate ion and the amounts of deliquescent which may be included in a stable solution of the invention may be approximately determined by averaging from the specific test data set forth above and hereinafter for the particular ingredients.

Thus, for approximately 2.7 percent by weight of deliquescent material, for any of the three propionate salts, ammonium, sodium or potassium, or any combination thereof, and for any of the preferred five deliquescent materials or any combination thereof, applicant has found that a stable solution of the invention can always be formulated with at least approximately 30 percent by weight of propionate salt.

Also, for approximately 2.7 percent by weight of deliquescent material, applicant's test data indicates that an upper limit of approximately 68 percent by weight equivalent of propionic acid may be included in a stable solution of the invention by proper selection of the salt of propionic acid and the deliquescent material or various combinations thereof.

It is presently preferred to embody at least approximately 1.0 percent by weight of deliquescent material in the solution of the present invention to assure adequate mold inhibiting and dust inhibiting functioning of the product in various climates, including adequate water anti-migration capability. Applicant's tests indicate that approximately the following percentages by weight equivalent of propionic acid (of which 98.65 percent by weight is propionate ion) can be included in a stable product according to the invention where the amount of deliquescent material is 1.0 percent:

For ammonium propionate as the salt of propionic acid, approximately 64 percent with calcium chloride deliquescent, and approximately 73 percent with magnesium chloride, ferric chloride, manganese chloride, or zinc chloride deliquescent materials.

For sodium propionate as the salt of propionic acid, approximately 35 percent with calcium chloride deliquescent, and approximately 73 percent with magnesium chloride, ferric chloride, manganese chloride, or zinc chloride deliquescent materials.

For potassium propionate as the salt of propionic acid, approximately 46 percent with calcium chloride deliquescent, approximately 67 percent with magnesium chloride or manganese chloride deliquescent, approximately 73 percent with ferric chloride deliquescent, and approximately 62 percent with zinc chloride deliquescent.

Thus, for approximately 1.0 percent by weight of deliquescent material, for any of the three propionate salts, ammonium, sodium, or potassium, or any combination thereof, and for any of the preferred five deliquescent materials or any combination thereof, applicant's tests indicate that a stable solution of the invention can always be formulated with at least approximately 35 percent by weight of propionate salt.

Also, for approximately 1.0 percent by weight of deliquescent material, applicant's test data indicates that an upper limit of approximately 73 percent by weight equivalent of propionic acid may be included in a stable solution of the invention by proper selection of the salt of propionic acid and the deliquescent material or various combinations thereof.

To provide a guide for those skilled in the art in the selection of one or more of the five preferred deliquescent materials to be included in the solution, applicant conducted tests determining the relative proportions of each of the five preferred deliquescent materials which could be contained in a stable solution product of the invention for a selected percent by weight equivalent of propionic acid in the solution.

With ammonium propionate as the salt of propionic acid, for 55 percent by weight equivalent of propionic acid, the following percentages by weight of the five deliquescent materials which could be contained in a stable solution were:
Calcium chloride between 4.0 and 5.0 percent
Magnesium chloride between 7.0 and 8.0 percent
Ferric chloride between 8.0 and 9.0 percent
Manganese chloride between 7.0 and 8.0 percent
Zinc chloride between 9.0 and 10.0 percent.

With sodium propionate as the salt of propionic acid, and 36.7 percent by weight equivalent of propionic acid, the following percentages by weight of the five deliquescent materials which could be contained in a stable solution were:
Calcium chloride between 0.5 and 1.0 percent
Magnesium chloride between 11.0 and 12.0 percent
Ferric chloride between 0.5 and 1.0 percent
Manganese chloride between 13.0 and 14.0 percent
Zinc chloride between 1.0 and 2.0 percent.

With potassium propionate as the salt of propionic acid, and 30 percent by weight equivalent of propionic acid, the following percentages by weight of the five preferred deliquescent materials which could be included in a stable solution were:
Calcium chloride between 3.0 and 4.0 percent
Magnesium chloride between 7.0 and 8.0 percent
Ferric chloride between 7.0 and 8.0 percent
Manganese chloride between 8.0 and 9.0 percent
Zinc chloride between 8.0 and 9.0 percent.

It is apparent from the foregoing that the use of calcium chloride as the deliquescent material places a considerable limitation on the amount of propionate ion which can be contained in the solution. Nevertheless, an adequate percentage of propionate ion together with an adequate percentage of calcium chloride can be embodied in the solution of the invention for satisfactory operation of the invention in most circumstances.

Tests conducted by applicant indicate somewhat better performance of calcium chloride as a deliquescent than the other four preferred deliquescent materials, at least on a relative short-term basis, which appears to be a compensating factor making use of calcium chloride more acceptable as the deliquescent material in the present invention.

Lower Limits for Propionate Ions

Applicant is not aware of any physical basis for a specific lower limit of the percent by weight equivalent of propionic acid to be included in the solution product of the invention. Nevertheless, it is presently preferred to include at least approximately 20 percent by weight equivalent of propionic acid (of which 98.65 percent by weight is propionate ion) to assure that the product is effective as a mold and dust inhibitor under all conditions of operation. Below approximately 20 percent, the propionic salt becomes rapidly functionally and economically ineffective for performing its intended functions of inhibiting both mold and dust. It is the upper limits of propionic ion content which are important since it is preferred to include close to the maximum possible percent by weight of propionic ion content in the solution of the invention for maximum mold-inhibiting performance of the invention.

Upper Limits for the Deliquescent Material

It is preferred to not include more than approximately 10 percent deliquescent material in the solution product of the invention. Greater than 10 percent deliquescent material undesirably limits the amount of propionic ion which may be made available in the formulation, and therefore limits the basic mold-inhibiting performance which is available from the product. Nevertheless, applicant's tests indicate that up to approximately 20 percent 35 deliquescent material may be included in the product of the invention without seriously impairing the performance of the product, although it would then be necessary to undesirably limit the percent by weight of propionate ion available in the product, particularly where the deliquescent material is calcium chloride. Any amount greater than approximately 20 percent by weight of the deliquescent material would be entirely nonutilitarian, and in very humid climates there would be an undesirable tendency for the product of the invention to take on moisture from the humid atmosphere.

Lower Limits for the Deliquescent Material

Applicant has not determined any physical basis for a specific lower limit of the percentage by weight of deliquescent material to be included in the solution product of the invention. 0.5 percent by weight of deliquescent material appears to provide satisfactory operation of the invention for most circumstances. At least approximately 1.0 percent deliquescent material is presently preferred to assure adequate operation of the invention for both mold and dust inhibiting under the various climatic conditions where the product is likely to be utilized. At least approximately 2.7 percent by weight deliquescent material is a presently most preferred amount to assure against loss of moisture and consequent dust problems under very dry climate conditions, and to assure against moisture migration where very wide day/night temperature variations might otherwise tend to cause moisture buildup adjacent feed or grain container walls. A presently preferred amount of deliquescent material in the product is approximately 3.6 percent.

Humectant

The humectant is preferably any one or more humectants from the group consisting of glycerol, potassium polymetaphosphate, propylene glycol, sorbitol, triacetin, mannitol, pectins, and polyhydric alcohols. The preferred range for the amount of humectant in the product, regardless of which one or more humectants may be included, is from approximately 1.0 percent to approximately 4.0 percent by weight. Within this range, applicant has found that the humectant does not appreciably change the amounts or proportions of propionate ions and deliquescent material which may be included in a stable solution of the invention as indicated in the test results presented above.

Monosodium Glutamate

The presently preferred range for MSG is from approximately 1.15 percent to approximately 3.45 percent by weight (from approximately 1 percent to approximately 3 percent by weight for the glutamic acid if the MSG is made in the process as in the first process example given hereinafter). Inclusion of MSG in the product is only recommended where the product of the invention is to be used in hog feed. Addition of MSG to the product of the invention does not materially change the amounts and proportions of propionate ion and deliquescent material which may be included in the product of the invention as indicated by the test data set forth hereinabove.

Method for Producing the Invention

The method for producing the product of the invention is believed most clearly understandable by a description of the production of specific batch weights of the product with the ingredients in relative proportions that will produce a satisfactory embodiment of the product.

EXAMPLE 1

The total batch weight for the first example given is 300 lbs., and the product to be produced is an aqueous solution of sodium propionate in which the humectant is glycerine, and which includes MSG. In this example, the MSG will be made during the process by including hydrochloric acid and glutamic acid among the ingredients.

For this 300 lb. batch, the ingredients and amounts thereof by weight are as follows:
26.5 lbs. water
3.3 lbs. "concentrated" hydrochloric acid, [HCl]
3.6 lbs. 100% glutamic acid $HOOC(CH_2)_2CH(NH_2)COOH$
7.25 lbs. 100% glycerine
3.0 lbs. deliquescent material consisting of 1.5 lbs. magnesium chloride, 1.0 lb. calcium chloride, 0.3 lb. manganese chloride, 0.1 lb. ferric chloride, and 0.1 lb. zinc chloride
110.0 lbs. 50% sodium hydroxide [NaOH]
146.35 lbs. 100% propionic acid $CH_3CH_2COOH$ The hydrochloric acid and glutamic acid are added to the water before the water is added to another of the ingredients except possibly the glycerine, and this will produce glutamic acid monohydrochloride, as follows:

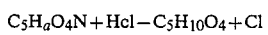

$$C_5H_aO_4N + Hcl - C_5H_{10}O_4 + Cl$$

The glycerine is added to the water, preferably after the hydrochloric acid and glutamic acid have been added; but if desired, the glycerine may be added to the water before the hydrochloric acid and glutamic acid.

The deliquescent material is added to the water, preferably after the hydrochloric acid and glutamic acid have been added; but if desired, the deliquescent material may be added to the water before the hydrochloric acid and glutamic acid.

Then, preferably the next step is to dilute the propionic acid with the water which already contains the glutamic acid monohydrochloride and the glycerine and deliquescent material, and then the sodium hydroxide is added to the mixture. Alternatively, the sodium hydroxide may be diluted with the water which contains the glutamic acid monohydrochloride, and then the propionic acid added to this mixture. The first of these two alternatives is preferred, because when the water is added to the sodium hydroxide, a large amount of heat is generated, and by having the large quantity of propionic acid already present when the sodium hydroxide is added, the propionic acid will serve as a heat sink and the thermal activity will be reduced.

The chemical reaction of the propionic acid with the sodium hydroxide is as follows:

Propionic Acid + Sodium Hydroxide → Sodium
    Propionate + Water or

CH₃CH₂COOH + NaOH → CH₃CH₂COO⁻Na⁺ + H₂O

In preparing a sodium propionate solution with high propionate ion concentration as is desirable for the present invention, applicant has found that when sodium hydroxide is added directly to propionic acid there is a serious precipitation problem. However, by placing all of the other ingredients, including the water, glycerine, hydrochloric acid and glutamic acid, in one of the solutions before the sodium hydroxide and propionic acid are brought together, the number of molecules per unit of space has already been diluted out sufficiently to produce a solution after completion of the acid/base reaction with all of the ingredients fully dissolved and with a high propionate ion concentration and long-term stability suitable for the purposes of the present invention.

During the reaction, the hydrochloric acid component of the glutamic acid monohydrochloride will be neutralized by the sodium hydroxide and thereby removed from the glutamic acid, and the glutamic acid will react with the sodium hydroxide to produce MSG, as follows:

Glutamic Acid + Sodium Hydroxide → Monosodium
    Glutamate + Water or

C₅H₉O₄N + NaOH → C₅H₈O₄ⁿ⁻Na⁺ + H₂O

For this 300 lbs. batch example, there is 48.4 percent propionic acid by weight, of which 98.65 percent by weight is propionate ion. Thus, in the product of the invention that is produced in this example, there is 48.14 percent by weight of propionate ion.

If the MSG is to be added as MSG instead of being formed during the process by getting it into solution with hydrochloric acid and reacting it with sodium hydroxide, then the MSG is preferably added to the water before the water is combined with the other ingredients of the product. For the foregoing 300 lbs. batch, the 3.6 lbs. of glutamic acid used in the formulation will result in 4.14 lbs. of MSG in the final product. Accordingly, if the MSG is not made during the process but added at the end of the formulating procedure, 4.14 lbs. of MSG will be added to make the 300 lb. batch formulation in this example. In that case, without the presence of hydrochloric acid as one of the ingredients, in order to neutralize the product, 3.7 lbs. less of sodium hydroxide will be used, and then to make up the same batch weight and relative amounts of the ingredients in the batch, water will be added in the amount of 3.7 lbs. Such water is preferably added prior to the mixing together of the sodium hydroxide and propionic acid in accordance with the procedure referred to above of diluting out the number of molecules per unit of space as much as possible to work against precipitation.

In the final product, the sodium propionate ionizes in the solution to become:

(CH₃CH²COO⁻Na⁺

It is this propionate ion which is the effective mold inhibitor in the product, and it inhibits mold in the same way and with the same efficacy as the corresponding propionate ion does in propionic acid, but without the offensive odor and corrosiveness of the propionic acid.

It is to be understood that in the preparation of this first example as described above, the ingredients are to be mixed as required at the various stages.

The percentages by weight of active ingredients in this first example are approximately 48.14 percent propionate ion, 1.0 percent deliquescent material, 2.42 percent humectant, and 1.38 percent MSG, and this first example product has a pH of approximately 6.6.

EXAMPLE 2

Applicant has prepared a 100 lb. batch of the product of the invention. The ingredients for this batch were:
10.8 lbs. water
1.3 lbs. 100% MSG
2.3 lbs. 100% glycerin
1.0 lb. deliquescent material, consisting of approximately 0.5 lb. magnesium chloride, 0.33 lb. calcium chloride, 0.1 lb. magnesium chloride, 0.033 lb. ferric chloride, and 0.033 lb. zinc chloride
36.4 lbs. 50% sodium hydroxide
48.2 lbs. 100% propionic acid First, the MSG was mixed and dissolved in the water. Then the glycerine and deliquescent material were added to the water and mixed. Then the sodium hydroxide was added to the water/MSG/sodium hydroxide and mixed. Finally, the propionic acid was added to the other ingredients and mixed. The reaction was then allowed to proceed to completion, resulting in a mold-inhibiting product according to the invention having the following relative proportions by weight of the ingredients:
47.55% propionate ion
1.0 % deliquescent material
2.3 % humectant
1.3 % MSG It will be noted that some water was added in each of the above two examples. In order to provide the solution product of the present invention with maximum propionate ion content, water need not be deliberately added as in these two examples, because sufficient water for a satisfactory aqueous solution will automatically be produced in the reaction when the ingredients are mixed, from the 50 percent hydroxide component of the mixture, and also because water is a reaction product between the acid and the base. The water in the aqueous solution product enables the salt of propionic acid in the product to be substantially uniformly dispersed when the product is applied to the feed. The water also maintains the salt of propionic acid in hydrolyzed condition so that the propionate ion component of the solution is enabled to most efficiently perform its function as a mold inhibitor.

In summary, the aqueous solution product of the present invention is the first completely satisfactory mold-inhibiting product of which applicant is aware for use with animal feed grains, the product having no objectionable odor or corrosion characteristics, so that the product is comfortable to use and should be acceptable on a worldwide basis. The product of the invention has been found experimentally to be fully acceptable by even the most sensitive animals such as hogs, and will not contaminate workers with any objectionable odor. In addition to its excellent mold-inhibiting characteristics, the product of the invention also has surprising and synergistic dust-inhibiting characteristics which solve heretofore very serious dust problems in connection with animal feed, poultry litter, and grain elevators.

It is to be understood that although the present invention has been described hereinabove primarily for use in connection with feed, grain, and poultry litter mold and dust problems, the invention is fully applicable to a variety of other mold and dust problems. Accordingly, the invention is not intended to be limited to use in connection with the specific examples described herein.

While the present invention has been described herein in what are conceived to be the most practical and preferred embodiments, it is recognized that departures may be made therefrom within the scope of the invention, which is therefore not to be limited to the details disclosed herein, but is to be accorded the full scope of the appended claims.

What is claimed is:

1. A grain composition formulated for storage in a metal storage container comprising at least one grain and an effective mold-inhibiting and dust generation inhibiting amount of a stable aqueous liquid composition comprising an effective mold inhibiting amount of at least one edible propionate salt, an effective moisture migration inhibiting and propionate anion stabilizing amount of at least one edible deliquescent substance.

2. A grain composition according to claim 1, wherein said liquid composition further comprises an effective moisture stabilization and propionate stabilization enhancing amount of at least one edible humectant.

3. A grain composition according to claim 2, wherein said liquid composition has a pH in the range of from about 6.3 to about 6.9.

4. A grain composition according to claim 2, wherein said humectant comprises at least one humectant selected from the group consisting of glycerol, potassium polymetaphosphate, propylene glycol, sorbitol, triacetin, mannitol, pectins, and polyhydric alcohols.

5. A grain composition according to claim 1, wherein said liquid composition has a pH of from about 6.3 to about 6.9.

6. A grain composition according to claim 1, wherein said propionate salt comprises at least one salt of propionic acid selected from the group consisting of ammonium propionate, sodium propionate, and potassium propionate.

7. A grain composition according to claim 1, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

8. A grain composition according to claim 1, wherein said deliquescent substance comprise at least one deliquescent substance selected from the group consisting of magnesium chloride, calcium chloride, manganese chloride, ferric chloride, and zinc chloride.

9. A method of inhibiting non-uniform accumulations of moisture in grain animal feed or hay adjacent the walls of a metal storage container subject to large day/night temperature variations, said method comprising the step of applying to said grain, animal feed or hay prior to introducing said grain, animal feed or hay into said metal container an effective moisture migration inhibiting amount of a stable aqueous liquid composition comprising at least one edible propionate salt, at least one edible deliquescent substance.

10. A method according to claim 9, wherein said liquid composition further comprises a moisture stabilization enhancing amount of at least one edible humectant.

11. A method according to claim 10, wherein said liquid composition has a pH in the range of from about 6.3 to about 6.9.

12. A method according to claim 10, wherein said humectant comprises at least one humectant selected from the group consisting of glycerol, potassium polymetaphosphate, propylene glycol, sorbitol, triacetin, mannitol, pectins, and polyhydric alcohols.

13. A method according to claim 9, wherein said liquid composition has a pH in the range of from about 6.3 to about 6.9.

14. A method according to claim 9, wherein said propionate salt comprises at least one salt of propionic acid selected from the group consisting of ammonium propionate, sodium propionate, and potassium propionate.

15. A method according to claim 9, wherein said deliquescent substance comprises at least one deliquescent substance selected from the group consisting of ammonium citrate, calcium, chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium oxide, potassium phosphate, sodium bisulphate, stannic sulphate, and zinc chloride.

16. A method according to claim 9, wherein said deliquescent substance comprises at least one deliquescent substance selected from the group consisting of magnesium chloride, calcium chloride, manganese chloride, ferric chloride, and zinc chloride.

\* \* \* \* \*